United States Patent [19]

Ressemann et al.

[11] Patent Number: 5,980,484
[45] Date of Patent: Nov. 9, 1999

[54] DILATION BALLOON FOR A SINGLE OPERATOR EXCHANGE CATHETER OR SIMILAR DEVICE

[75] Inventors: Thomas V. Ressemann, St. Cloud; Timothy Stivland, Plymouth; David Blaeser, Champlin, all of Minn.

[73] Assignee: SciMed Life Systems, Inc., Maple Grove, Minn.

[21] Appl. No.: 09/024,073

[22] Filed: Feb. 17, 1998

Related U.S. Application Data

[60] Continuation of application No. 08/635,446, Apr. 19, 1996, Pat. No. 5,718,683, which is a division of application No. 08/567,810, Dec. 6, 1995, Pat. No. 5,549,553, which is a continuation of application No. 08/055,009, Apr. 29, 1993, abandoned.

[51] Int. Cl.$^6$ .................................................. A61M 29/00
[52] U.S. Cl. ............................ 604/96; 604/523; 606/194
[58] Field of Search .......................... 604/96–103, 523, 604/524, 528, 532, 539; 606/192–196

[56] References Cited

U.S. PATENT DOCUMENTS

| | | | |
|---|---|---|---|
| 3,834,394 | 9/1974 | Hunter et al. | 128/325 |
| 4,295,464 | 10/1981 | Shihata | 128/1 R |
| 4,490,421 | 12/1984 | Levy | 428/35 |
| 4,576,142 | 3/1986 | Schiff | 128/1 D |
| 4,601,713 | 7/1986 | Fuqua | 604/280 |
| 4,644,936 | 2/1987 | Schiff | 128/1 D |
| 4,697,573 | 10/1987 | Schiff | 128/1 D |
| 4,710,181 | 12/1987 | Fuqua | 604/280 |
| 4,738,666 | 4/1988 | Fuqua | 604/280 |
| 4,762,129 | 8/1988 | Bonzel | 128/344 |
| 4,798,193 | 1/1989 | Giesy et al. | 128/7 |
| 4,881,547 | 11/1989 | Danforth | 128/344 |
| 4,909,252 | 3/1990 | Goldberger | 606/194 |
| 4,944,745 | 7/1990 | Sogard et al. | 606/194 |
| 4,958,634 | 9/1990 | Jang | 606/194 |
| 4,983,167 | 1/1991 | Sahota | 606/194 |
| 5,000,734 | 3/1991 | Boussignac et al. | 604/96 |
| 5,002,531 | 3/1991 | Bonzel | 604/96 |
| 5,019,042 | 5/1991 | Sahota | 604/101 |
| 5,049,131 | 9/1991 | Deuss | 604/96 |
| 5,078,685 | 1/1992 | Colliver | 604/96 |
| 5,085,662 | 2/1992 | Willard | 606/159 |
| 5,090,958 | 2/1992 | Sahota | 604/98 |
| 5,147,377 | 9/1992 | Sahota | 606/194 |
| 5,160,321 | 11/1992 | Sahota | 604/96 |
| 5,180,367 | 1/1993 | Kontos et al. | 604/101 |
| 5,180,370 | 1/1993 | Walinsky | 604/96 |
| 5,232,446 | 8/1993 | Arney | 604/96 |
| 5,320,605 | 6/1994 | Sahota | 604/101 |
| 5,338,300 | 8/1994 | Cox | 604/96 |
| 5,368,567 | 11/1994 | Lee | 604/102 |
| 5,380,319 | 1/1995 | Saito et al. | 606/28 |
| 5,383,890 | 1/1995 | Miraki et al. | 606/194 |
| 5,409,458 | 4/1995 | Khairkhahan et al. | 604/96 |
| 5,549,553 | 8/1996 | Ressemann et al. | 604/96 |
| 5,718,683 | 2/1998 | Ressemann et al. | 604/96 |
| B1 4,762,129 | 7/1991 | Bonzel | 606/194 |

FOREIGN PATENT DOCUMENTS

| | | |
|---|---|---|
| 611 582 A1 | 8/1994 | European Pat. Off. . |
| WO 94/11048 | 5/1994 | WIPO . |
| WO 94/11053 | 5/1994 | WIPO . |

*Primary Examiner*—John D. Yasko
*Attorney, Agent, or Firm*—Crompton, Seager & Tufte, LLC

[57] ABSTRACT

An intravascular balloon catheter including a dilation balloon is provided. The intravascular balloon catheter includes a shaft assembly including a proximal end, a distal end, and an inflation lumen extending longitudinally therethrough. The dilation balloon is operably coupled proximate the distal end of the shaft assembly, such that an interior chamber of the dilation balloon is in fluid communication with the inflation lumen. In one aspect of the invention, a core wire is disposed within the inflation lumen of the shaft assembly. In another aspect of the invention, a tubular member extends longitudinally over the exterior of the dilation balloon for receiving a guidewire.

14 Claims, 8 Drawing Sheets

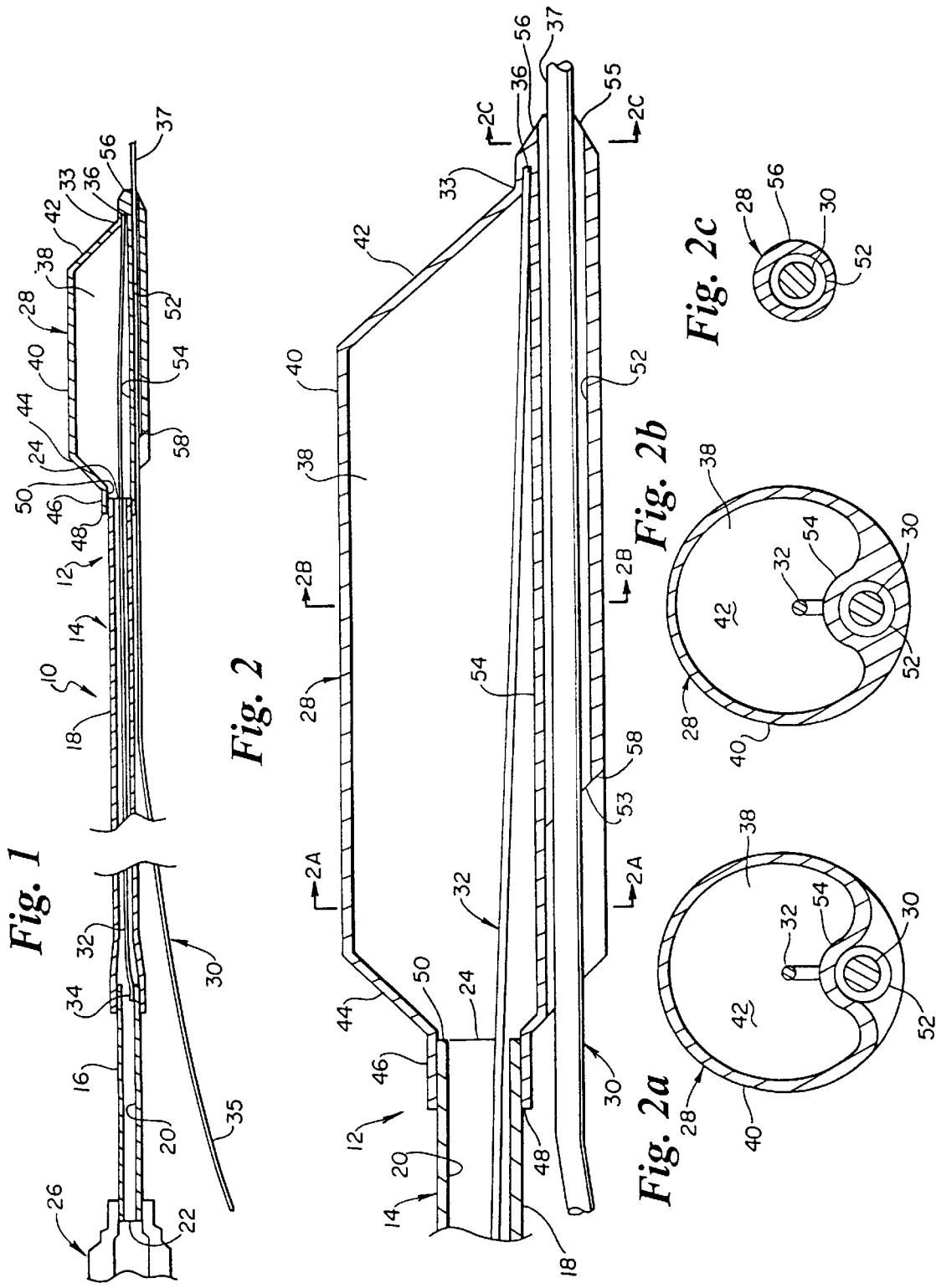

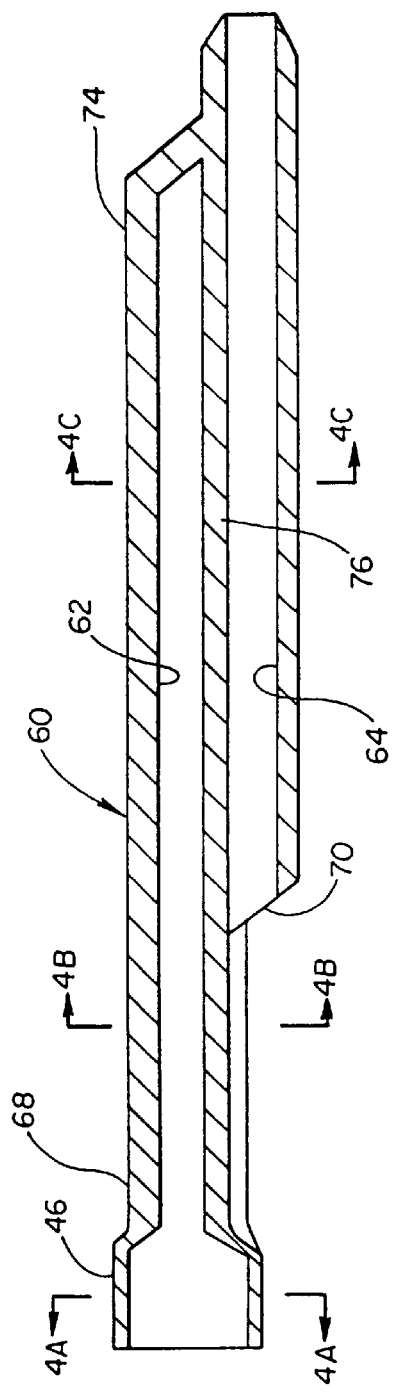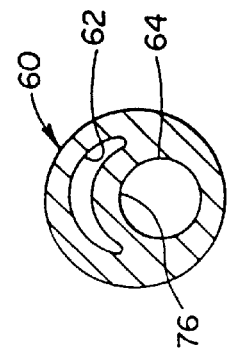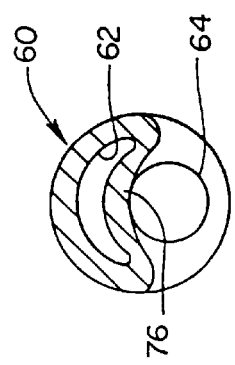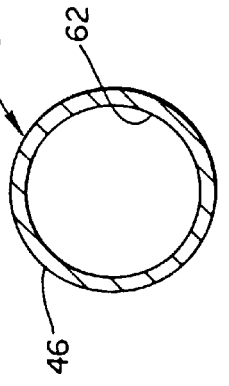

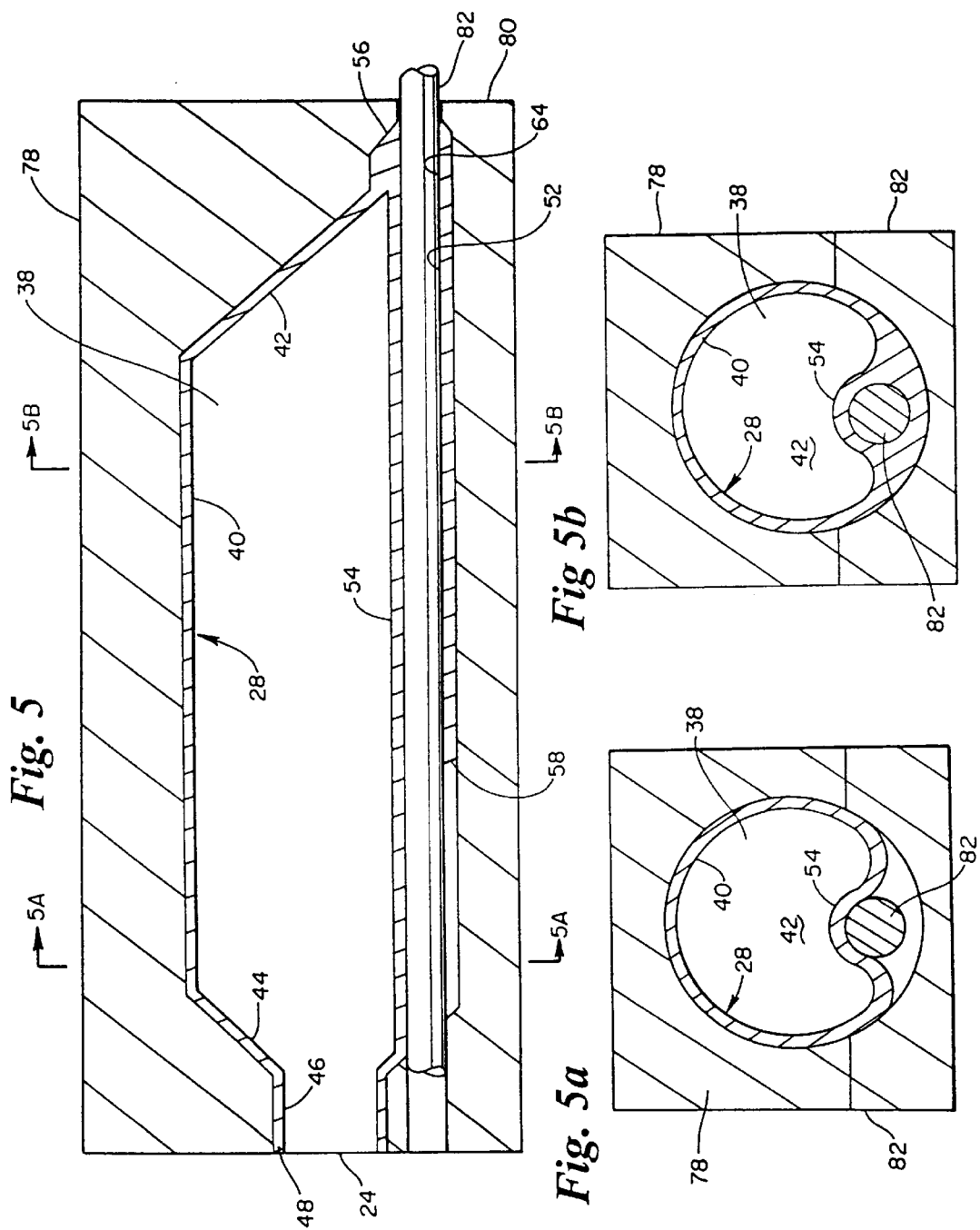

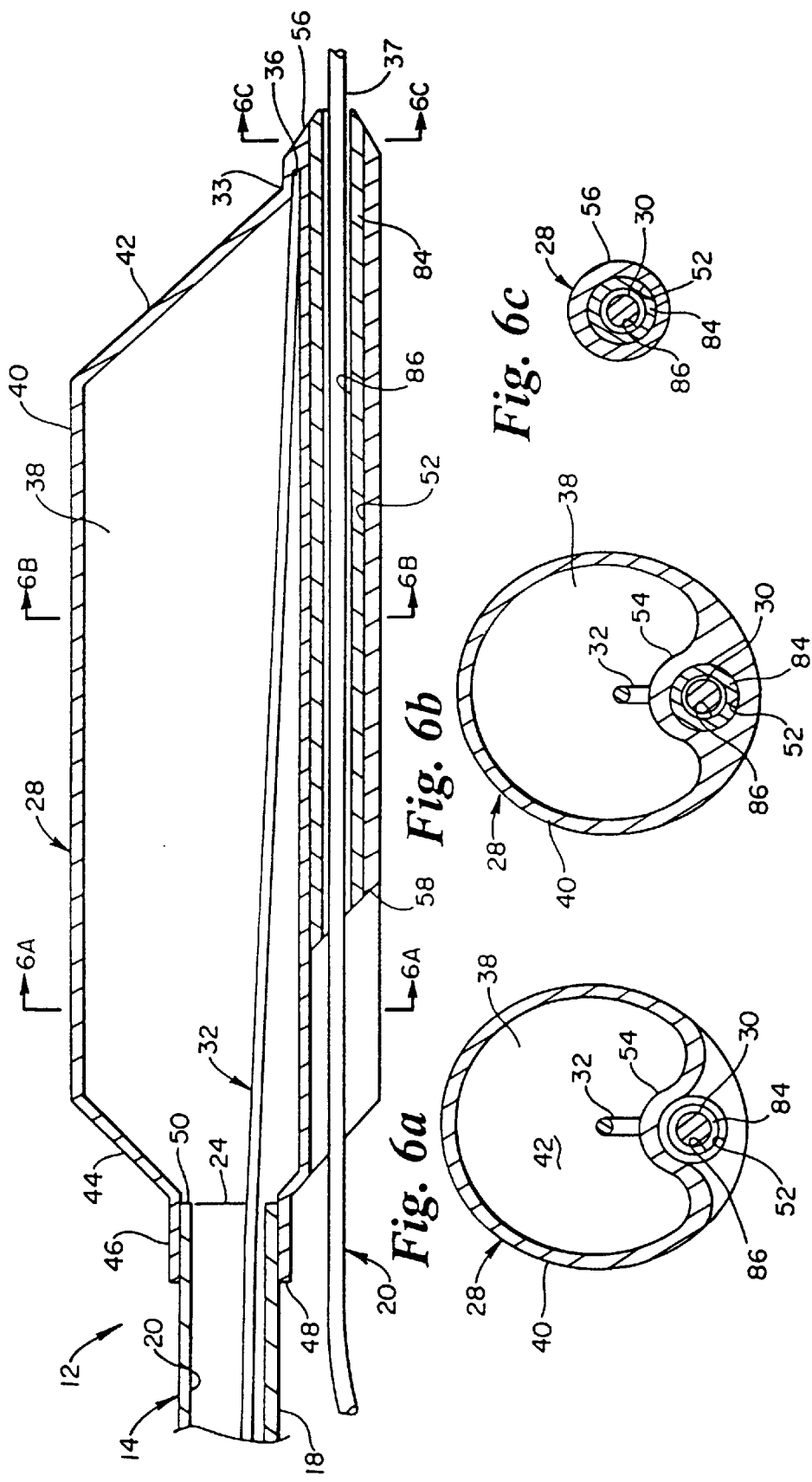

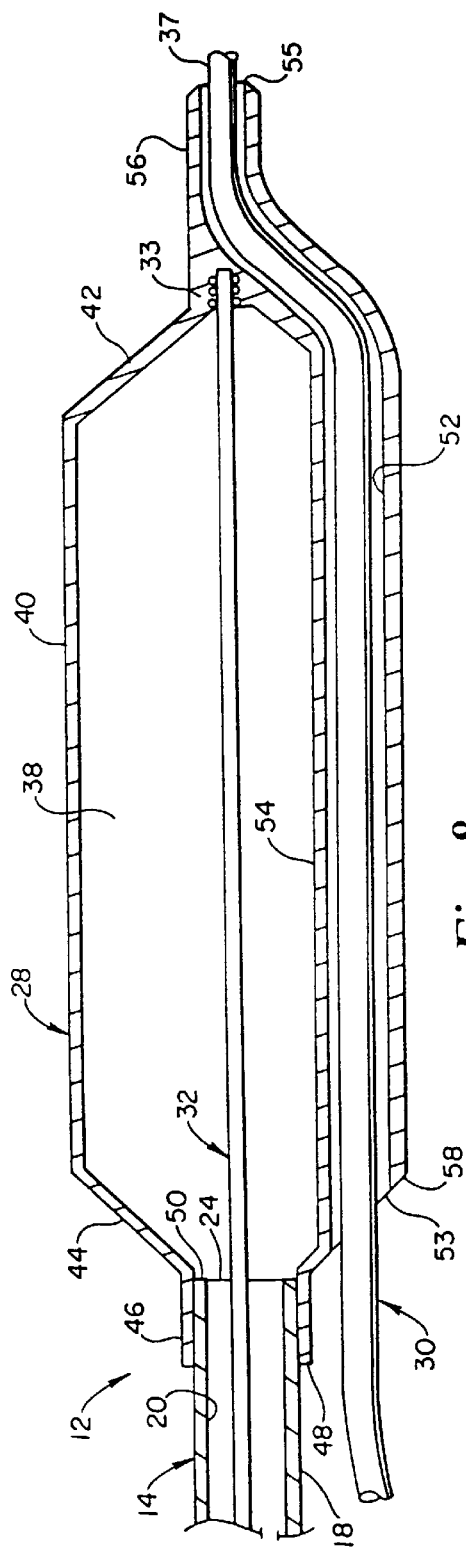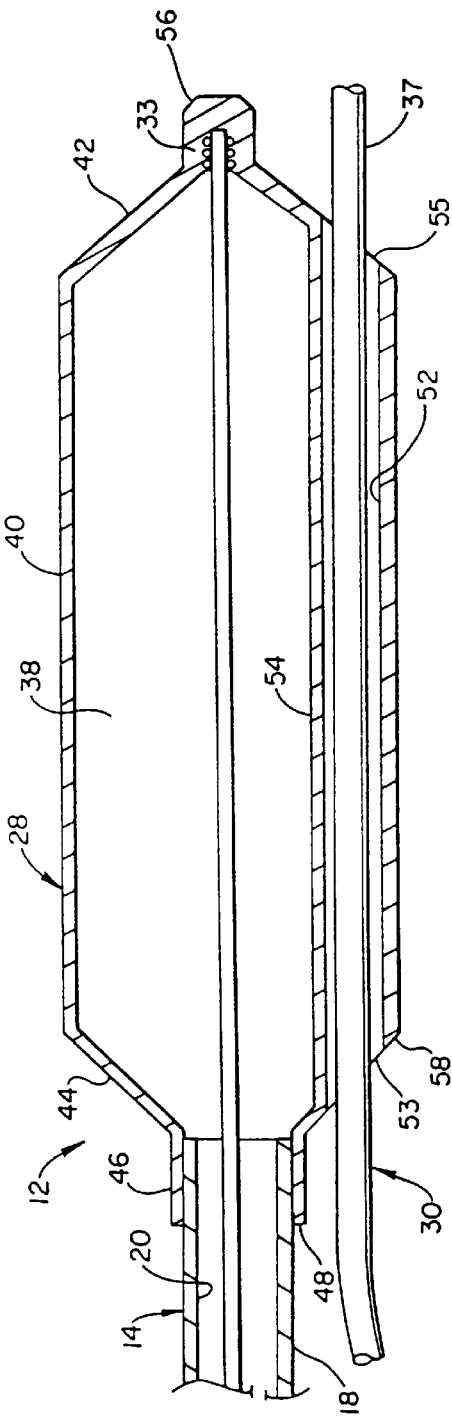

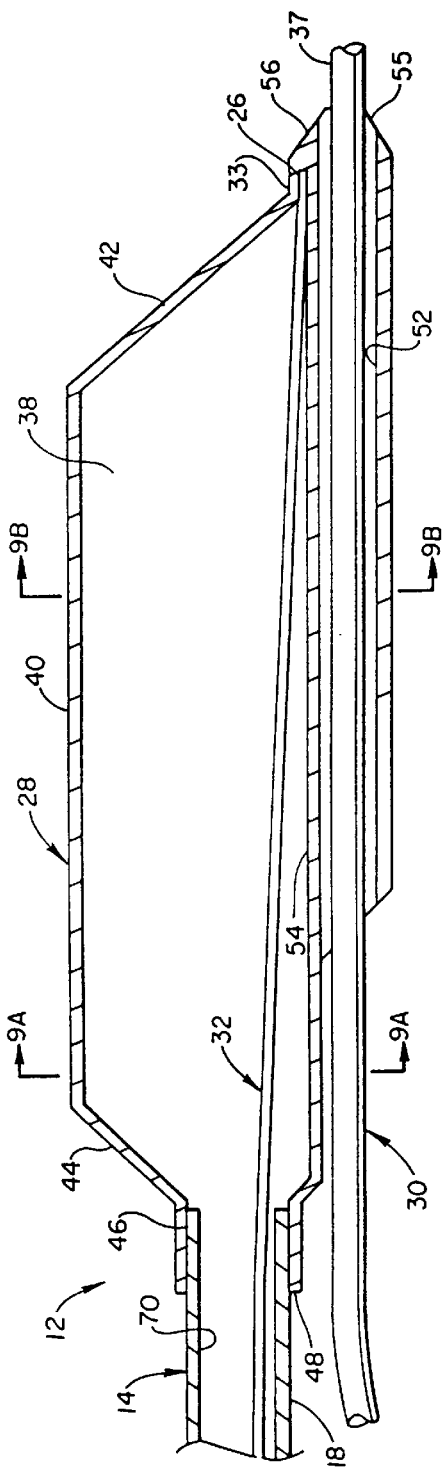
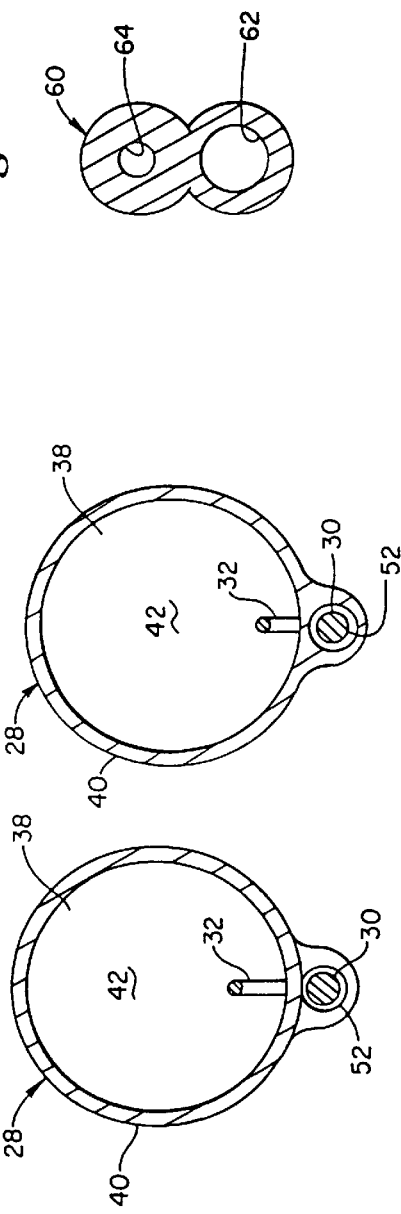

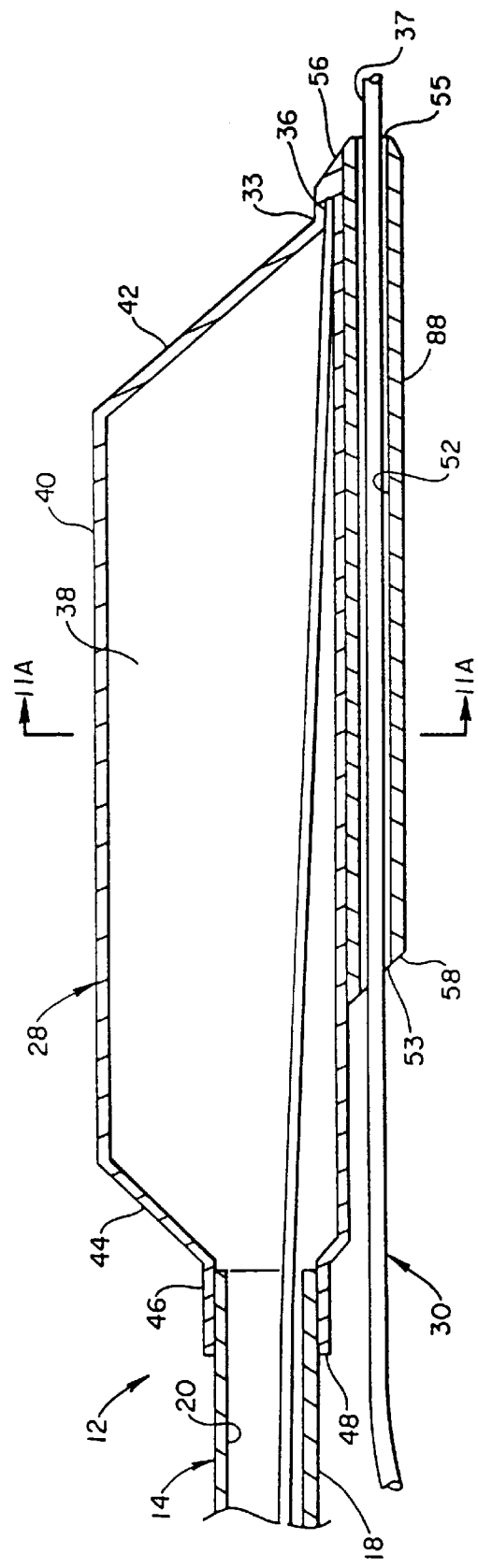
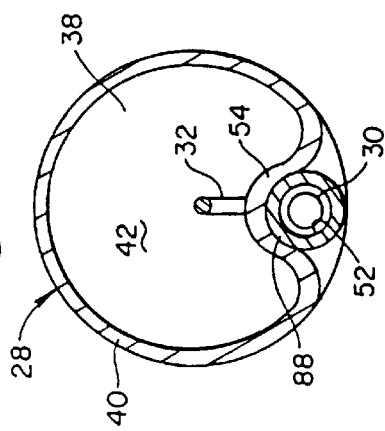

DILATION BALLOON FOR A SINGLE OPERATOR EXCHANGE CATHETER OR SIMILAR DEVICE

This application is a continuation of application Ser. No. 08/635,446, filed Apr. 19, 1996, now U.S. Pat. No. 5,718,683 which in turn is a divisional of application Ser. No. 08/567,810, filed Dec. 6, 1995, now U.S. Pat. No. 5,549,553 which in turn is a continuation of application Ser. No. 08/055,009, filed Apr. 29, 1993 now abonded.

BACKGROUND OF THE INVENTION

The present invention relates generally to devices used in intravascular therapeutic and diagnostic procedures, and more particularly, to a dilation balloon for a single operator exchange catheter.

Intravascular catheterization devices have proven to be useful and efficient for both therapeutic and diagnostic purposes. Intravascular therapeutic techniques, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic techniques, such as ultrasonic imaging and Doppler blood flow measurements, have been developed to measure or image the extent of an occlusion of a vessel (e.g. stenosis). The devices used to perform the aforementioned intravascular therapeutic and diagnostic techniques may be used together or in conjunction with more invasive techniques such as coronary surgery.

These intravascular therapeutic and diagnostic devices have achieved acceptance because of their effectiveness as well as the fact that they can be used in a minor surgical procedure that is relatively non-disruptive to the patient compared to coronary surgery. These devices rely on the positioning of a catheter into the vascular system of a patient via an incision at an accessible location which may be remote from the site of the occlusion or stenosis. For example, the accessible location may be the femoral artery at the groin. The intravascular device is then advanced through the incision via the femoral artery to a desired coronary distal site. The distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is often a need for intravascular catheters of very low profile that can be positioned in narrow, tortuous regions of a person's vasculature.

Another important consideration relating to intravascular procedures, such as angioplasty, relates to the exchange of various devices used to perform the procedures. Intravascular therapeutic and diagnostic devices come in various types and sizes suitable for the vessel size and location in which the treatment is to be performed. Sometimes, it becomes necessary to exchange a first therapeutic device for one of a different size after an unsuccessful attempt has been made to position the first device in the appropriate location. It may also become necessary to exchange therapeutic devices after the first device is successfully positioned in the desired location. This may be necessitated because it becomes apparent that the first device is the wrong size or configuration, or because it is determined that additional therapeutic or diagnostic procedures with a different size or type of device is required.

Several different types of catheter constructions have been developed for positioning intravascular therapeutic or diagnostic catheters through a patient's vasculature. One type of catheter design, commonly referred to as a fixed-wire type catheter, includes a non-removable wire tip attached on a distal end of the intravascular catheter. The wire tip facilitates maneuvering the catheter to the desired vessel site. A disadvantage of the fixed-wire type catheter is that if it becomes necessary to exchange a first catheter for a second catheter, the maneuvering procedure must be repeated for the second catheter. As mentioned above, this can sometimes be a tedious and difficult procedure.

Another type of catheter design, referred to as an over-the-wire type catheter, includes a central lumen through the intravascular device that can accommodate a separate guide wire that is movable, and removable, in relation to the catheter to facilitate positioning the catheter in a remote vessel location over the guide wire. In the over-the-wire construction, the catheter typically includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel. The guide wire may then be withdrawn proximally through the lumen of the catheter or may be left in place extending from the distal end of the catheter during the procedure.

The over-the-wire type intravascular catheter facilitates exchanges because a first catheter can be exchanged with a second catheter without removing the guide wire. This allows an exchange of catheters without having to repeat the difficult and time consuming task of positioning the guide wire. In order to leave the distal end of the guide wire in place, it is preferred to maintain a hold on a proximal end portion of the guide wire during the exchange operation. One way to maintain such a hold is to use a guide wire having a sufficiently long length (e.g. 300 cm) so that the entire catheter can be completely withdrawn over the guide wire while maintaining a hold on a portion of the wire. A disadvantage of this method is that the long proximally extending portion of the guide wire may be in the way during the procedure. Another way to maintain a hold on a portion of the guide wire during an exchange operation is to use a guide wire extension. A disadvantage of this method is that not all guide wires are adapted to connect to an extension wire, and moreover, the step of connecting the guide wire to the extension wire can sometimes be tedious and difficult to perform.

A variation of the over-the-wire type catheter which facilitates the exchange a first catheter with a second catheter is the single-operator exchange type construction. With the single-operator exchange type construction, a guide wire occupies a position adjacent and exterior to the intravascular catheter along proximal and middle portions of the catheter. Typically, the guide wire enters into a guide wire lumen which is attached to a shaft of the catheter and often extends through the balloon. With this type of construction, the catheter can be positioned in the patient's vessel by positioning a guide wire in the desired location and advancing the catheter device over the wire. In the event it becomes necessary to exchange the catheter, the position of the guide wire can be maintained during withdrawal of the catheter without the use of a long guide wire (e.g. 300 cm) or an extension wire. Because the proximal end of the guide wire is exterior to the catheter, the guide wire can be held during withdrawal of the catheter so that the position of the distal end of the guide wire in the patient's vessel can be maintained. With this type of catheter, it is desirable to minimize the length of the guide wire lumen to decrease frictional forces acting on the guide wire, thus facilitating the trackability of the catheter over the guide wire. One disadvantage of some single-operator exchange type devices is the increased profile of the balloon resulting from a separate guide wire lumen extending therethrough. As noted above, it is desirable to minimize the profile of the balloon to allow positioning in narrow, tortuous regions of a person's vasculature.

With both fixed wire and over-the-wire type catheters, an introducer sheath and/or a guiding catheter may also be employed. An introducer sheath is used to provide translumenal access to the femoral artery or another appropriate location. Then, with the access provided by the introducer sheath, a guide catheter may be positioned in the patient's vessel. The guide catheter may be advanced at least part of the way to the desired site, such as to the aortic arch. The guide catheter has an internal lumen through which the intravascular device, including the guide wire in an over-the-wire construction, is advanced. One of the functions of the guide catheter is to support the device. The guide catheter may be approximately 100 to 106 cm in length. Alternatively, in certain situations, e.g., if positioning of the device does not involve traversing tortuous vessel passages, a guide catheter may be employed to position an intravascular device without the use of a guide wire.

Accordingly, there is a need for an improved single-operator exchange type catheter which minimizes the profile of the balloon and facilitates trackability of the catheter over the guide wire.

SUMMARY OF THE INVENTION

Briefly stated, the present invention is directed to a dilation balloon for a single-operator exchange type catheter. The catheter includes an elongated shaft having a proximal portion, a distal portion, and an inflation lumen extending therethrough. In one aspect of the invention, the dilation balloon includes a balloon member having a chamber therein in fluid communication with the inflation lumen. The balloon member defines a portion of a guide wire lumen which coextends with a portion of the balloon member for receiving a guide wire. In another aspect of the invention, the guide wire lumen is spaced exteriorly from the shaft. In yet another aspect of the invention, a process for making a dilation balloon includes the step of providing a longitudinal member having a first elongated lumen and a second elongated lumen. A first portion of the longitudinal member which defines the first lumen is blow molded into an inflatable balloon which defines an interior chamber for receiving inflation fluid. A second portion of the longitudinal member which defines the second lumen is blow molded into a longitudinal rib which defines a guide wire lumen coextending with said chamber.

Preferably, the guide wire lumen is formed in a side wall of the balloon member which defines the interior chamber. The side wall has a longitudinal rib protruding inwardly therefrom which defines the guide wire lumen, although the rib can protrude outwardly from the side wall of the balloon member. A proximal end of the guide wire lumen terminates distally of a proximal end of the inflation chamber. A tubular insert, preferably in the form of a coil, can also be positioned within the guide wire lumen to inhibit deformation of the lumen when the balloon is inflated. Also preferably, the balloon member has only one opening therethrough in communication with the chamber and a distal end of the shaft is adjacent the opening.

The process for making the dilation balloon preferably includes the step of extruding a polymeric element into a longitudinal member having first and second elongated lumens. Internal pressure is applied within the second lumen, and the longitudinal member is heated to allow expansion of the longitudinal member. A tubular member, preferably in the form of a coil, is inserted into the second lumen. Internal pressure is then applied within the first lumen, and the longitudinal member is heated to allow expansion of the member against a mold portion. The second lumen contracts as a result of the expansion of the first lumen, and the longitudinal member is allowed to cool while the internal pressure is applied to deform the longitudinal member into a balloon member having an interior chamber for receiving inflation fluid. Preferably, a portion of the longitudinal member is severed so that the guide wire lumen is shorter than the balloon member.

The present invention provides significant advantages over other single-operator exchange type balloon catheters. When a first catheter is exchanged for a second catheter, the relatively short guide wire lumen in the balloon minimizes the friction acting on the guide wire to facilitate the withdrawal and advancement of the catheters over the guide wire. The single-operator exchange type configuration allows an operator to maintain a hold on the guide wire while exchanging the catheter, thus avoiding the use of a long guide wire or a guide wire extension. The profile of the balloon may also be minimized because the guide wire lumen is formed in the balloon wall rather than in a separate tube extending through the interior chamber of the balloon. In addition, the catheter shaft need not extend through the interior chamber of the balloon to deliver inflation fluid or provide structural support for the guide wire lumen. The guide wire lumen of the present invention may also be more secure than other known single-operator exchange type catheters which typically have a separate tube adhesively bonded to the catheter shaft and balloon. Moreover, it may be less costly to manufacture the catheter of the present invention.

Accordingly, the present invention provides a single-operator exchange type catheter which minimizes the profile of the balloon and facilitates trackability of the catheter over the guide wire.

The present invention, together with further objects and advantages, will be best understood by reference to the following detailed description taken in conjunction with the accompanying drawings.

BRIEF DESCRIPTION OF THE DRAWINGS

FIG. 1 is a longitudinal sectional view of a preferred embodiment of a balloon dilation catheter of the present invention.

FIG. 2 is a longitudinal sectional view of a distal portion of the catheter shown in FIG. 1.

FIGS. 2A–2C are cross-sectional views of the catheter taken along the corresponding lines 2A—2A, 2B—2B and 2C—2C in FIG. 2.

FIG. 4 is a longitudinal sectional view of the longitudinal member in FIG. 3 showing the formation of a proximal neck portion of the balloon.

FIGS. 4A–4C are cross-sectional views of the longitudinal member taken along the corresponding lines 4A—4A, 4B—4B and 4C—4C in FIG. 4.

FIG. 5 is a longitudinal sectional view of the longitudinal member showing a portion of the balloon blow-molded against first and second mold portions.

FIGS. 5A and 5B are cross-sectional views of the balloon and mold portions taken along the lines 5A—5A and 5B—5B in FIG. 5.

FIG. 6 is a longitudinal sectional view of a second preferred embodiment of a balloon dilation catheter.

FIGS. 6A–6C are cross-sectional views of the catheter taken along the corresponding lines 6A—6A, 6B—6B and 6C—6C in FIG. 6.

FIG. 7 is a longitudinal sectional view of a third preferred embodiment of a balloon dilation catheter.

FIG. 8 is a longitudinal sectional view of a fourth preferred embodiment of a balloon dilation catheter.

FIG. 9 is a longitudinal sectional view of a fifth preferred embodiment of a balloon dilation catheter.

FIGS. 9A and 9B are cross-sectional views of the catheter taken along the lines 9A—9A and 9B—9B in FIG. 9.

FIG. 10 is a cross-sectional view of a dual lumen longitudinal member used to form the balloon shown in FIG. 9.

FIG. 11 is a longitudinal sectional view of a sixth preferred embodiment of a balloon dilation catheter.

FIG. 11A is a cross-sectional view of the catheter taken along the line 11A—11A in FIG. 11.

DETAILED DESCRIPTION OF THE PREFERRED EMBODIMENTS

Figure 3:
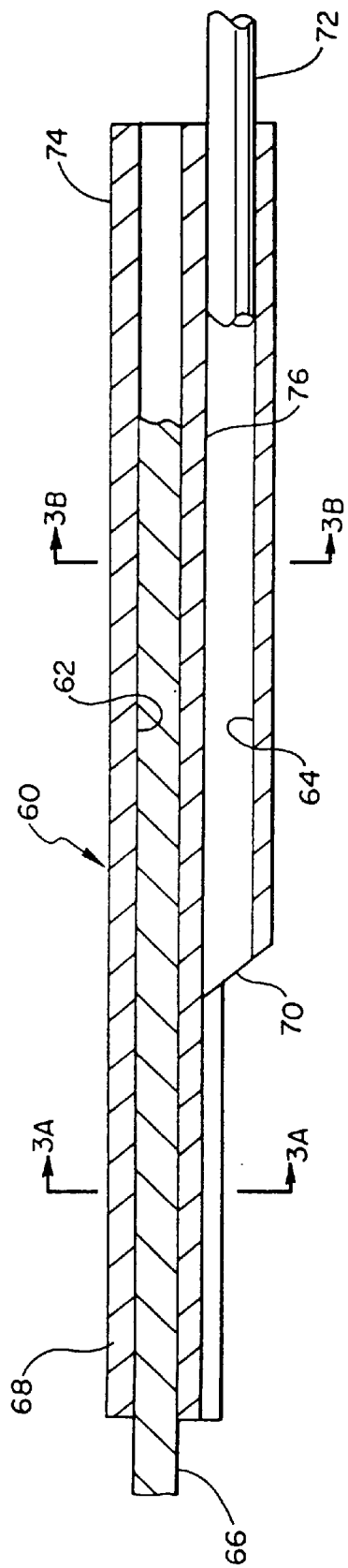
FIG. 3 is a longitudinal sectional view of a dual lumen longitudinal member used to form the balloon in FIG. 2.
Figure 3B:
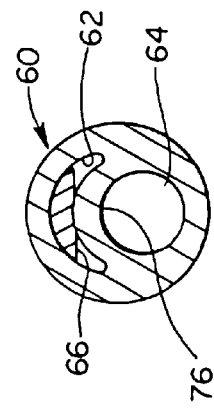
FIGS. 3A and 3B are cross-sectional views of the longitudinal member taken along the corresponding lines 3A—3A and 3B—3B in FIG. 3.
Figure 3A:
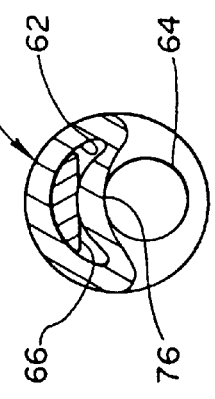

The presently preferred embodiments and methodology described herein are applicable to coronary angioplasty procedures and are specifically described in the context of dilation balloon catheters. It should be understood, however, that the embodiments and methodology of the present invention may be adapted for use with other types of intravascular therapeutic devices, such as atherectomy catheters, as well as diagnostic catheters, such as ultrasonic or laser catheters.

Referring to FIG. 1, a first preferred embodiment of a single-operator exchange type intravascular apparatus is indicated generally at 10. The intravascular apparatus 10 includes a balloon dilation catheter 12 having an elongated shaft 14. A proximal portion 16 of the shaft 14 is adapted to extend outside the body of a patient during use, and a distal portion 18 of the shaft 14 is positionable intravascularly during use by manipulation of the proximal portion 16. The shaft 14 includes an inflation lumen 20 extending therethrough and has a proximal opening 22 and a distal opening 24. A manifold 26 is connected to the proximal portion 16 of the shaft 14 and a dilation balloon 28 is connected to the distal portion 18 of the shaft 14 in fluid communication with the inflation lumen 20. Inflation fluid is conveyed via the lumen 20 from the manifold 26 to inflate the balloon 28 and therefore dilate a vessel in a conventional manner known in the art.

Preferably, the shaft 14 has a length of approximately 135 cm and an inner diameter of approximately 0.0210 inches which defines the inflation lumen 20. To provide greater stiffness for manipulation of the shaft 14, the proximal portion 16 is made of stainless steel hypodermic tubing having an outer diameter of about 0.023 inches. The proximal portion 16 of the shaft 14 can also be configured as a coil spring which is pre-loaded a desired amount to vary the flexibility of the shaft. The distal portion 18 of shaft 14 has an outer diameter of about 0.025 inches and is formed of a relatively flexible polymeric material, such as a polyolefin copolymer or polyethylene, to allow the shaft 14 to easily track through a vessel. A stiffening wire 32, preferably about 0.005 inches in diameter, is also provided to facilitate manipulation of the catheter 12. The stiffening wire 32 extends longitudinally through the inflation lumen 20 of the shaft 14 and through the balloon 28 to a distal end 33 of the balloon 28. A proximal end 34 of the stiffening wire 32 is attached to the proximal portion 16 of the shaft 14 and a tapered distal end 36 is attached to the distal end 33 of the balloon 28. A spring coil tip can be secured about the distal end 36 of the stiffening wire 32, and a radiopaque marker (not shown) can be mounted about the wire 32 within the interior chamber 38 of the balloon 28 for tracing the position of the balloon as the catheter 12 is inserted into the patient via fluoroscopy. A catheter shaft incorporating the foregoing features is disclosed in U.S. patent application Ser. No. 07/833,099, filed Feb. 10, 1992, now U.S. Pat. No. 5,395,332 the disclosure of which is specifically incorporated herein by reference. The stiffening wire 32 can be attached to the shaft 14 and balloon 28 in any suitable manner known in the art. For example, the distal end 36 of the wire 32 can be secured to a distal end of the shaft 14 or a proximal portion of the balloon 28.

The guide wire 30 coextends exteriorly of the shaft 14 to provide a single-operator exchange construction. The guide wire 30 has a sufficient length, preferably about 160–190 cm, so that a proximal portion 35 of the guide wire 30 can extend outside the body of a patient while a distal portion 37 extends distally of the balloon 28 during use. The guide wire 30 can have an outer diameter between 0.008 and 0.022 inches, although conventional guide wires typically have a diameter of 0.010, 0.014 or 0.018 inches.

The dilation balloon 28 is connected to the distal portion 18 of the catheter shaft 14. The balloon 28 can be formed from a polyolefin copolymer or other polymer material. For example, in one embodiment, the balloon 28 is formed of a polyolefin copolymer (such as that sold by DuPont under the tradename SURLYN as Resin No. 8527) using secondary treatment with 5 to 50 Mega-rad electron beam irradiation to enhance strength in the region of the balloon 28. The balloon 28 has an interior chamber 38 defined by a side wall 40, a tapered distal end wall 42, and a substantially conical proximal end wall 44. The walls 40, 42 and 44 preferably have a thickness of about 0.002 inches and the balloon 28 has an outer diameter of about 0.100 inches when inflated. A proximal neck portion 46 extends proximally from the conical end wall 44 of the balloon 28 and defines an opening 48 for receiving the catheter shaft 14. Thus, the catheter shaft 14 is adhesively secured to the neck portion 46 and the inflation lumen 20 is in fluid communication with the interior chamber 38 of the balloon 28 for delivering fluid to the balloon. Preferably, the neck portion 46 defines the only opening in the balloon 28 which communicates with the interior chamber 38, and a distal end 50 of the catheter shaft 14 is located adjacent the neck portion 46. Because the shaft 14 does not extend through the interior chamber 38 of the balloon 28 and the balloon does not have a distal neck portion for receiving the shaft, the profile of the balloon is minimized to allow insertion through a relatively narrow passage in a vessel.

To facilitate the operation and exchange of the catheter 12, a guide wire lumen 52 is formed in the side wall 40 of the balloon 28 for receiving the guide wire 30. The guide wire lumen 52 coextends longitudinally with a portion of the balloon 28 and has a uniform cross-section terminating in a proximal opening 53 and a distal opening 55. When a 0.014 inch guide wire is used, the inner diameter of the guide wire lumen 52 is preferably about 0.0167 inches. Because the guide wire lumen 52 is formed in the side wall 40 of the balloon 28, the shaft 14 does not have to extend through the interior chamber 38 to provide structural support for the guide wire lumen. Preferably, the side wall 40 is formed such that a longitudinal rib 54 protrudes inwardly therefrom to define the guide wire lumen 52. As best shown in FIG. 2B, this configuration allows the balloon 28 to inflate to a substantially cylindrical shape when filled with inflation fluid, which tends to provide a more uniform deformation of a stenosis in an angioplasty procedure. To further reduce the profile of the balloon 28, the distal end wall 42 of the balloon 28 tapers to a distally extending tip portion 56 which forms part of the rib 54. The diameter of the distal tip portion 56 is preferably about 0.029 inches in diameter when a 0.014 inch guide wire is used. In addition, a distal portion of the proximal neck 46 of the balloon 28 can converge inwardly to reduce the profile of the balloon 28 at that portion of the neck 46 and allow the axis of the guide wire lumen 52 to be closer to the axis of the catheter shaft 14 and the neck portion 46.

The formation of the guide wire lumen 52 in the side wall 40 of the balloon 28 also facilitates trackability of the catheter 12 over the guide wire 30 because the length of the guide wire lumen 52 is shorter than the guide wire tubes of other known catheters which typically extend through the entire balloon or even proximally into the shaft. The reduction in length decreases frictional forces acting on the guide wire 30 when the catheter 12 is advanced or withdrawn over the guide wire. As shown in FIG. 2, a proximal beveled end 58 of the guide wire lumen 52 can be spaced distally from the proximal end wall 44 of balloon 28 a desired amount to further reduce the length of the guide wire lumen 52. A distal end of the guide wire lumen 52 can also be spaced proximally from the distal end wall 42 of the balloon 28. As shown in FIGS. 7 and 8,. for example, the guide wire lumen 52 can also coextend with the entire length of the side wall 40 such that the proximal end 58 of the lumen 52 terminates at the proximal end wall 44 of the balloon 28. In any of the embodiments described herein, the guide wire lumen 52 can have a low friction coating, such as Teflon®, on an inner surface thereof to further enhance movement of the balloon 28 over the guide wire 30. Alternatively, the coating may be made of other materials such as a hydrophilic or silicone coating. In addition to or instead of the low friction coating, a metallic or foil coating may also be incorporated on the inner surface of the guide wire lumen 52.

FIGS. 3–5C illustrate the process for making the dilation balloon of the present invention. A cylindrical longitudinal member 60, preferably about 0.0232 inches in diameter, is initially extruded with a first elongated lumen 62 and a second elongated lumen 64 formed therein. As noted above, the longitudinal member 60 is made of a polyolefin copolymer or other polymeric material. The first lumen 62 has a generally "crescent moon" shaped cross-section which will form the interior chamber 38 of the balloon 28. The second lumen 64 has a generally circular cross-section which will form the guide wire lumen 52 of the balloon 28. For use with a 0.025 inch guide wire, the width between the ends of the crescent moon shaped first lumen 62 is preferably about 0.0148 inches, and the inner diameter of the second lumen 64 is preferably about 0.0165 inches. To allow a lower proximal portion of the member 60 to be severed, a mandrel 66 is positioned within the first lumen 62. The lower proximal portion of the member 60 is then cut as shown in FIG. 3 to define a desired length of the second lumen 64 (i.e. guide wire lumen 52).

To form the proximal neck portion 46 of the balloon 28, the mandrel 66 is withdrawn and heat is applied to the upper proximal end portion 68 of member 60 to soften the polymer material. The end portion 68 is stretched in order to receive a cylindrical mandrel (not shown) sized to correspond to the desired inner diameter of the proximal neck portion 46 of the balloon 28. The end portion 68 is then allowed to cool and contract around the cylindrical mandrel to form the desired size and shape of the neck portion 46. Alternatively, a radially inwardly directed force is can be applied via a necking die in a known manner (not shown) to force the softened material about the cylindrical mandrel. Such a force causes the length of the proximal end portion 68 of the member 60 to extend while the material is forced inwardly against the cylindrical mandrel. Also alternatively, the proximal neck portion 46 of the balloon 28 can be formed in a blow molding process which is described below rather than the foregoing stretching and necking process.

To close a distal end 70 of the first lumen, a rod 72 is inserted into the second lumen 64 and an upper distal end portion 74 of the member 60 is heated and necked down against an intermediate wall 76 of member 60. The intermediate wall 76 defines the first and second lumens 62 and 64 and ultimately becomes the longitudinal rib 54 and distal tip 56 of the balloon 28.

The longitudinal member 60 is then placed in first and second mold portions 78 and 80, and a rod 82 having the desired inner diameter of the guide wire lumen 52 is inserted into the second lumen 64 of member 60. The balloon 28 is then blow molded into the shape shown in FIGS. 5–5C by applying internal pressure within the first lumen 62 and heating corresponding portions of member 60 with an air or water bath. The material is thereby softened to allow radial expansion of the material outwardly against the mold portions 78 and 80 to form the walls 40, 42 and 44 of the balloon 28. The material is then allowed to cool while the interior chamber 38 is pressurized so that the balloon 28 will regain the desired shape when inflated. The rod 82 is then withdrawn from the newly formed guide wire lumen 52 which is defined by the longitudinal rib 54.

Alternatively, the rib 54 can be prestressed by an initial molding process prior to molding the walls 40, 42 and 44 of the balloon 28. In such a process, the mandrel 66 is inserted into the first lumen 62 of member 60 and internal pressure is applied within the second lumen 64. The material surrounding the second lumen 64 is then heated by an air or water bath and allowed to expand. The rod 82 is inserted into the second lumen 64, the material is allowed to cool and contract around the rod 82, and the rod 82 is removed to form a prestressed rib 54. Also alternatively, the material can be forced radially inwardly about the rod 82 by the subsequent blow molding of the remaining portion of the balloon or by other adequate means. As a result, distortion of the guide wire lumen 52 and rib 54 is less likely during subsequent formation of the balloon 28 or during inflation of the balloon in an angioplasty procedure.

FIGS. 6–11 illustrate alternative embodiments of the present invention. Since these embodiments are similar to the previously described embodiment, similar parts appearing in FIGS. 5–11 are represented by the same, corresponding reference numeral.

In FIG. 6, a tubular insert 84 is positioned within the guide wire lumen 52 to prevent deformation of the guide wire lumen 52 and rib 54 when the balloon 28 is inflated. The insert 84 is preferably the same length as the guide wire lumen 52 and has a lumen 86 extending therethrough sized to receive the guide wire 30. The insert 84 can be made of a polymeric material, such as polyimide, and preferably has a low friction coating on an inner surface thereof as described above. Alternatively, the insert 84 can be made of other materials, such as polyurethane, polyethylene, polyester, or other polymers. The insert 84 can also be made of a polyimide-teflon composite material, or reinforced with wire or a braid of metal or plastic or other materials. Alternatively, the insert 84 can be a coil wire preferably about 0.001 or 0.002 inches in diameter and made of stainless steel, platinum, or the like. A radiopaque marker (not shown) can also be mounted about the coil insert 84 for tracing the position of the balloon via fluoroscopy as the catheter 12 is inserted into the patient. To make the embodiment of the balloon 28 shown in FIG. 6, the insert 84 can be molded with the rib 52 rather than removing the rod 82 as described above. In addition, an adhesive can be applied to an inner wall of the guide wire lumen 52 or to the insert 84 before the material contracts around the insert 84 to further bond the insert 84 within the guide wire lumen 52.

In FIG. 7, the distal end wall 42 of balloon 28 is substantially conical and the distal tip portion 56 is substantially aligned with the axis of the balloon 28 and the catheter shaft 14. In addition, the guide wire lumen 52 is formed in the distal end wall 42 and curves upwardly so as to coextend with the end wall 42 and distal tip portion 56. The embodiment in FIG. 8 is similar to the one in FIG. 7, but the guide wire lumen 52 has a substantially uniform cross-section and does not coextend with the end wall 42 or distal tip portion 56. In addition, the guide wire lumen 54 extends along the entire length of the side wall 40 in these embodiments.

In FIG. 9, the longitudinal rib 54 protrudes outwardly from the side wall 40 of the balloon 28 rather than inwardly. This embodiment is formed in the same manner as the aforementioned embodiments, but the extruded longitudinal member 60 has a figure "8" shaped cross-section with generally circular first and second lumens 62 and 64 (FIG. 10).

In FIG. 11, the guide wire lumen 52 is in the form of a separate tube 88 which is attached to an outer surface of the side wall 40 by a suitable adhesive. In this embodiment, a wrap of fibers or a soft elastic sheath (not shown) may also surround the balloon 28 and tube 86 to assist in maintaining the circular profile of the balloon 28 when inflated, and to assist in securing the tube 88 to the balloon 28.

In operation of the intravascular apparatus 10, intravascular access is initially made in a conventional manner. If the procedure is a percutaneous transluminal angioplasty (PCTA) procedure, access is made via the femoral artery. A conventional introducer and guide catheter (not shown) can be employed in a manner that is well known in the art. When used with the described embodiments of the present invention, a guide catheter should have a lumen of sufficient size to accommodate the catheter 12 and guide wire 30.

To initially position the catheter 12 in a patient's vessel, the guide wire 30 is preferably advanced to a desired location in a vessel. The proximal portion 35 of the guide wire 30 is then inserted into the guide wire lumen 52 of the balloon 28 and the catheter 12 is advanced distally to the desired location in the vessel. Alternatively, the catheter 12 can be advanced over the guide wire 30 prior to insertion in the vessel and the assembly can be advanced to a desired location in the vessel. As best shown in FIG. 1, a substantial portion of the guide wire 54 is positioned outside the catheter shaft 14 to allow a single-operator exchange of the catheter 12 for a second catheter. When a different size or configuration catheter is required, the catheter 12 is withdrawn so that the balloon 28 passes over the guide wire 30 while an operator maintains a hold on the proximal portion 35 of the guide wire 30. The balloon of a second catheter can then be advanced over the guide wire 30 to position the second catheter in the same location previously attained by the first balloon catheter 12. This single-operator exchange type configuration allows the operator to maintain a hold on the guide wire 30 without using an extension or a relatively long guide lumen and guide wire.

Thus, a single-operator exchange type catheter is provided which minimizes the profile of the balloon and facilitates trackability of the catheter over the guide wire.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the following claims, including all equivalents thereof, which are intended to define the scope of the invention.

I claim:

1. In an intravascular balloon catheter having a shaft assembly including a proximal end, a distal end, and an inflation lumen extending longitudinally therethrough, the improvement comprising:

a proximal shaft section having a lumen therethrough and a distal shaft section having a lumen therethrough, said proximal shaft section and said distal shaft section each having a proximal end and a distal end with said distal end of said proximal shaft section coupled to said proximal end of said distal shaft section to form said shaft assembly and said inflation lumen;

a dilatation balloon operably coupled proximate the distal end of the distal shaft section, said balloon having an exterior surface and an interior chamber therein, said interior chamber in fluid communication with said inflation lumen;

a core wire affixed within said proximal shaft section and extending distally therefrom within said inflation lumen; and a tubular member extending longitudinally over the exterior of said balloon for receiving a guide wire.

2. The catheter of claim 1, wherein the proximal shaft section is a hypotube.

3. The catheter of claim 1, wherein the tubular member is adjacent a side wall of the balloon.

4. The catheter of claim 1, wherein the tubular member extends beyond a distal end of the balloon.

5. The catheter of claim 1, wherein the balloon terminate in a distal hub, and the tubular member extends beyond the distal hub.

6. The catheter of claim 1, wherein said core wire terminates proximate a distal end of the balloon.

7. The catheter of claim 6, wherein the tubular member extends beyond a distal end of the core wire.

8. A catheter comprising:

a shaft assembly having a proximal end and a distal end, and an inflation lumen extending longitudinally therethrough, said shaft assembly including a proximal shaft section and a distal shaft section, each having a proximal end, a distal end and a lumen therethrough with said lumen of said proximal shaft section in fluid communication with said lumen of said distal shaft section to form said inflation lumen;

a balloon coupled proximate the distal end of the distal shaft section in fluid communication with the inflation lumen;

a core wire affixed within said proximal shaft section and extending distally within said inflation lumen; and a tubular member adjacent and exterior of the balloon for receiving a guide wire.

9. The catheter of claim 8, wherein the tubular member is coupled to the balloon.

10. The catheter of claim 8, wherein the tubular member is co-extending longitudinally with a portion of the balloon.

11. The catheter of claim 8, wherein the tubular member extends beyond a distal end of the balloon.

12. The catheter of claim 8, wherein the balloon terminates in a distal hub, and the tubular member extends beyond the distal hub.

13. The catheter of claim 8, wherein said core wire extends through at least a portion of said balloon.

14. The catheter of claim 13, wherein the tubular member extends beyond a distal end of the core wire.

* * * * *